(12) United States Patent
Joseph

(10) Patent No.: US 9,669,110 B2
(45) Date of Patent: Jun. 6, 2017

(54) METHOD FOR TIMING A COLONOSCOPY

(75) Inventor: Raymond E. Joseph, Gladwyne, PA (US)

(73) Assignee: Ferring B.V., Hoofddorp (NL)

( * ) Notice: Subject to any disclaimer, the term of this patent is extended or adjusted under 35 U.S.C. 154(b) by 133 days.

(21) Appl. No.: 13/549,889

(22) Filed: Jul. 16, 2012

(65) Prior Publication Data
US 2013/0018223 A1 Jan. 17, 2013

(51) Int. Cl.
- *A61K 33/08* (2006.01)
- *A61B 1/31* (2006.01)
- *A61P 1/10* (2006.01)
- *A61K 49/00* (2006.01)

(52) U.S. Cl.
CPC .................. *A61K 49/00* (2013.01)

(58) Field of Classification Search
CPC ...... A61K 9/009; A61K 49/00; Y10S 514/892
USPC .......................... 600/101; 424/692
See application file for complete search history.

(56) References Cited

U.S. PATENT DOCUMENTS

2011/0076339 A1* 3/2011 Vanner et al. ................ 424/605
2014/0087007 A1 3/2014 Cleveland et al.

OTHER PUBLICATIONS

J. A. Flemming Gastroenterology 2011.*
Aoun, Gastrointestinal Endoscopy 2005.*
Regev The Am. J. of Gastroenterology 1998.*
Araki, The Kurume Medical journal 1992.*
International Search Report and Written Opinion, PCT/US2012/046874 dated Nov. 22, 2012.
Flemming, J.A., "Split-Dose Picosalax is Superior to Traditional Dosing for Colonoscopy Preparation—A Randomized Control Trial", Gastroenterology, May 1, 2011, p. S-529. Retrieved from the Internet: URL: http://ac.els-cdn.com/S0016508511623585/1-s2.0-S0016508511623585-main.pdf?_tid=aa2d93f4-03bd-11e2-b55d-00000aacb361&acdnat=1348212571_316c3af91e3db00a9d3d9240008c1760 [retrieved on Sep. 21, 2012].
Heresbach et al., "Consensus in gastrointestinal endoscopy: preparation for full colonoscopy in 2011; Consensus en endoscopie digestive: preparation colique pour la coloscopie totale en 2011", ACTA Endoscopica, Springer-Verlag, Paris, vol. 41, No. 3, Mar. 31, 2011, pp. 145-152.
Spiegel et al., "Getting Ready for Your Colonoscopy", Mar. 14, 2011, Retrieved from the Internet: URL: http://www.researchcore.org/publications/docs/bookletlayout_printingversion.pdf [retrieved on Dec. 20, 2012].
Tjandra et al., "Oral Sodium Phosphate (Fleet®) is a Superior Colonoscopy Preparation to Picoprep® (Sodim Picosulfate-Based Preparation)" Diseases of the Colon & Rectum Springer-Verlag, NE, vol. 49, No. 5, Mar. 9, 2006, pp. 616-620.
Flemming et al., "Split-dose picosulfate, magnesium oxide, and citric acid solution markedly enhances colon cleansing before colonoscopy: a randomized, controlled trial", Gastrointestinal Endoscopy, vol. 75, No. 3, Mar. 1, 2012, pp. 537-544.
Church, Effectiveness of Polyethylene Glycol Antegrade Gut Lavage Bowel Preparation for Colonoscopy—Timing is the Key, Dis. Colon Rectum 1998, 41, 1223-25.
Huffman et al., Split-dose bowel preparation for colonoscopy and residual gastric fluid volume: an observational study, Gastronintest. Endosc., 2010, 72, 516-22.
Prieto-Frias et al., Split-dose sodium picosulfate-magnesium citrate colonoscopy preparation achieves lower residual gastric volume with higher cleansing effectiveness than a previous-day regimen, Gastrointest Endosc., 2016, 83(3), 566-73. (Epub Aug. 11, 2015).
Rex et al., Split-dose administration of a dual-action, low-volume bowel cleanser for colonoscopy: the See Clear I study, Gastronintest. Endosc., 2013, 78(1), 132-141.
Siddiqui et al., Duration of the interval between the completion of bowel preparation and the start of colonoscopy predicts bowel preparation quality, Gastrointest. Endosc., 2009, 69(3), 700-706.
Vanner et al., Timing and frequency of bowel activity in patients ingesting sodium picosulphate/magnesium citrate and adjuvant bisacodyl for colon cleansing before colonoscopy, Can. J. Gastroenterol., 2011, 25(12), 663-666.
Turner et al., Pico-Salax versus polyethylene glycol for bowel cleanout before colonoscopy in children: a randomized controlied trial, Endoscopy 2009, 41(12), 1038-1045, DOI: 10.1055/s-0029-1215333.
Japanese Patent Office, Notice of Reasons of Rejection for Japanese Application No. 2014-521688. dated Apr. 26, 2016, 3pp.

* cited by examiner

*Primary Examiner* — Suzanne Ziska
*Assistant Examiner* — Thurman Wheeler
(74) *Attorney, Agent, or Firm* — Fish & Richardson P.C.

(57) ABSTRACT

Based on the present disclosure, a minimal time interval can be achieved between the last ingestion of a picosulfate composition and the performance of the colonoscopy. For example, the present disclosure is directed to a method of timing a colonoscopy procedure performed on a patient in need thereof, comprising: administering, to the patient, a picosulfate bowel composition kit according to the kit's instructions; performing the procedure less than about 4 hours after the administration of the kit.

24 Claims, No Drawings

METHOD FOR TIMING A COLONOSCOPY

This application claims priority to U.S. Provisional Application No. 61/508,189 filed Jul. 15, 2011, which is incorporated herein by reference in its entirety.

Colorectal cancer (CRC) ranks third in incidence and second to third in case of cancer death for both men and women in the United States (US). Jackson-Thompson J, Ahmed F, German R R, et al. Cancer, Descriptive epidemiology of colorectal cancer in the United States, 1998-2001. 2006 Sep. 1; 107(5 Suppl):1103-11. The lifetime risk of being diagnosed with CRC is 5% to 6% with a 5-year survival rate of 60% to 70%. Regular screening, beginning at age 50 for average-risk individuals, is one of the keys to preventing colorectal cancer. Pignone M, Rich M, Teutsch S M, et al. Screening for colorectal cancer in adults at average risk: a summary of the evidence for the U.S. Preventive Services Task Force. Ann Int Med 2002; 137:132-141.

Several scientific organizations, including the US Preventive Services Task Force (USPSTF) and other federal agencies, recommend regular screening for all adults age 50 or older and at <45 years of age for African Americans. According to USPSTF, routine screening can reduce the number of people who die of colorectal cancer by as much as 60%. U.S. Preventive Services Task Force. Screening for Colorectal Cancer. Rockville, Md.: Agency for Healthcare Research Quality; 2002.

One of the initial colorectal cancer screening procedures is a fecal occult blood test. Approximately 2 of 100 fecal occult blood results are expected to be abnormal, requiring further investigation, most frequently a colonoscopy.

A colonoscopy is a minimally invasive endoscopic examination of the colon. Colonoscopies may provide a visual diagnosis (e.g., ulceration, polyps) and allow the opportunity for biopsy and removal of suspected lesions. Colonoscopies are used not only for colorectal cancer screening procedures but also used to investigate possible causes of abdominal pain, rectal bleeding, chronic constipation, chronic diarrhea, and other intestinal problems.

Colonoscopies or colorectal surgery requires the bowel to be as clear as possible with good preparation of the bowel before such procedures. The safety and efficacy of the procedure can be related to the quality of the pre-investigational bowel preparation: contamination of the colon with fecal material can lead to incomplete examination of the colonic mucosa or hinder the surgical procedures. Thus, inadequate bowel cleansing can lead to inaccurate results, as well as increasing the time it may take to conduct procedures and increasing the risk of complications. Similarly, for computed tomography colonography, any fluid or residue retained in the colon reduces sensitivity and specificity. Thus, the success of a colonoscopy is dependent, in part, upon an empty bowel, which allows for clear visualization of the colonic mucosa (including reaching the caecum) and completion of the colonoscopy. If a clear bowel is not achieved, the examination may need to be repeated; this creates a disruptive timing and rescheduling process for all: the patient, physician, and endoscopy staff.

Ideally, bowel-cleansing should clear the colon of most, of not all, solid material and cause no damage to the colonic mucosa. It should also be easy to administer, be well tolerated by the patient with few adverse events, and cause little shift in the patient's fluid and electrolyte balance. Bowel cleansing is not a pleasant procedure for the patient, yet compliance with any pre-treatment regimen is paramount. Therefore, pre-treatment with a bowel cleansing preparation should be suitable for the patient to self-administer with a minimum of inconvenience and of relatively short duration i.e., safe, simple, effective and pleasant tasting.

Prospective studies have reported that repeat colonoscopies due to the poor quality of bowel preparation are required in up to 6% of colonoscopy procedures. A more recent retrospective audit revealed a failure rate of 4.5%. Wexner S D, Garbus J E, Singh J J, et al. A prospective analysis of 13,580 colonoscopies: reevaluation of credentialing guidelines. Surg Endosc 2001; 15:251-61; Bowles C J A, Leicester R, Romaya C, et al. A prospective study of colonoscopy practice in the UK today: are we adequately prepared for national colorectal cancer screening tomorrow? Gut 2004; 53:277-82; Thomas-Gibson S, Tharpar C, Shah S G, et al. Colonoscopy at a combined district general hospital and specialist endoscopy unit: lessons from 505 consecutive examinations. J R Soc Med 2002;95:194-97; Thomson J, Phull P. Audit of bowel preparation with Pico-Salax (sodium picosulfate plus magnesium citrate) for colonoscopy. Int J Clin Pract 2006; 60(5):602-3. A retrospective review also showed that the scheduling of colonoscopies in the afternoon compared to morning may be a predictor of an incomplete colonoscopy and inadequate bowel preparation. Sanaka M et al., Afternoon colonoscopies have higher failure rates than morning colonoscopies, 101 Am. J. Gastroenerol. 2726-30 (2006).

In order to obtain consistently high quality colonoscopy examinations, one needs adequate colon cleansing. Enhancing the colonoscopy experience should also encourage more people to pursue examinations; consistent with public health goals of early polyp detection and removal of and accuracy of mucosal diagnosis. Currently available formulations can be improved, particularly regarding the timing requirements with complicated patient instructions leading to noncompliance and decreased incidences of lesion detection and therefore, repeat colonoscopies.

The present disclosure is directed to a method of timing a colonoscopy wherein the procedure is performed on the patient less than about 4 hours after the patient is administered a picosulfate bowel composition. For example, the present disclosure provides a method of timing a colonoscopy procedure performed on a patient in need thereof, comprising: administering, to the patient, a picosulfate bowel composition; and performing the procedure less than about 4 hours after the administration of the composition.

Another embodiment of the present disclosure provides a method of timing a colonoscopy procedure performed on a patient in need thereof, comprising: administering, to the patient, a picosulfate bowel composition less than about 4 hours before performing the procedure.

In a further embodiment, the present disclosure is directed to a method of timing a colonoscopy procedure performed on a patient in need thereof, comprising: administering, to the patient, a first bowel composition the day before the procedure; and administering, to the patient the day of the procedure, a second bowel composition; and performing the procedure less than about 4 hours after the administration of the second bowel composition.

The present disclosure is also directed to a method of timing a colonoscopy procedure performed on a patient in need thereof, comprising: administering, to the patient, a first bowel composition the day before the procedure; and administering, to the patient the day of the procedure, a second bowel composition less than about 4 hours prior to the procedure.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DESCRIPTION

Particular aspects of the disclosure are described in greater detail below. The terms and definitions as used in the present application and as clarified herein are intended to represent the meaning within the present disclosure. The patent and scientific literature referred to herein and referenced above are hereby incorporated by reference. The terms and definitions provided herein control, if in conflict with terms and/or definitions incorporated by reference.

Terms and Definitions

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency or value. With regard to specific values, it should be understood that specific values described herein for subject populations (e.g., the subject of the described clinical trial) represent median values, unless otherwise indicated as, e.g., mean values. Accordingly, aspects of the present disclosure requiring a particular value in a subject are substantially supported herein by population data in which the relevant value is assessed to be a meaningful delimitation of the subject population.

EXAMPLE

Clinical Study

I. Split-Dose Study: PicoPrep™ and HalfLytely® Comparison

Overall Clinical Study and Design: A clinical study comprising a randomized, assessor-blinded, multi-centered study investigating the efficacy, safety and tolerability of "Split-Dose" sodium picosulfate, magnesium oxide, and citric acid, for example PicoPrep™, for oral administration versus bisacodyl, polyethylene glycol 3350, sodium chloride, sodium bicarbonate, and potassium chloride, for example HalfLytely® for oral administration, for colon cleansing in preparation for colonoscopy. In addition to "split dose" administration of PicoPrep™ over Visit 1 and Visit 2, the PicoPrep™ administration also included where the first and second sachets of PicoPrep™ were both administered the day before the colonoscopy. The data presented in Table 4 includes the data obtained from both "split dose" administration methods.

This was planned to be 7-month, phase III, randomized, multi-center, assessor-blinded, parallel-group, active-control, non-inferiority study investigating the efficacy, safety, and tolerability of split-dose PicoPrep™ versus HalfLytely® for oral administration in adult subjects for colon cleansing in preparation for colonoscopy. The study was completed in 6 months.

The study was conducted at 10 investigative sites in the United States. It was planned that a sufficient number of subjects would be screened to ensure up to 600 randomized subjects (300 subjects to each treatment group). There were 608 subjects enrolled, 307 to the PicoPrep™ arm and 301 to the HalfLytely® arm; 599 subjects completed the study.

Treatment Administered

Subjects who fulfilled all inclusion and no exclusion criteria were randomized to one of the 2 preparations (PicoPrep™ or HalfLytely®) at Visit 2. On the day before the procedure (24 hours before), all subjects were limited to a liquid diet only; they received a list of clear liquids they were permitted to consume during the treatment. All assessments were performed at Visit 3. Subjects returned to the investigative site for 3 follow-up visits: within 24 to 48 hours (Visit 4), in 7 days (Visit 5), and in 4 weeks (Visit 6) after the colonoscopy procedure.

Only the subject and the sites' designated unblinded coordinator knew the treatment group to which each subject was randomized; the designated unblinded coordinator instructed the subject in use of the bowel preparation at Visit 2. It is important to note that treatment was also blinded to the gastroenterologist who assessed the efficacy of the 2 tested preparations.

PicoPrep™

PicoPrep™ powder for oral solution consisted of 2-sachets administered in divided doses (i.e., a picosulfate bowel composition kit). PicoPrep™ was reconstituted by mixing the contents of a sachet in a cup with 5 oz. of cold water. Subjects randomized to the PicoPrep™ treatment group began receiving treatment (first reconstituted sachet) between 5:00 PM and 9:00 PM 1 day before colonoscopy (Visit 2). Following the first administration of PicoPrep™, subjects consumed five 8 oz. glasses of clear liquids and following the second administration, subjects consumed three 8 oz. glasses of clear liquids. Subjects completed receiving treatment (second reconstituted sachet) the next day (Visit 3) at least 5 hours prior to but no later than 9 hours prior to colonoscopy.

HalfLytely®

HalfLytely® powder form for oral solution consisted of powder for oral solution (two 5 mg bisacodyl tablets+2 liters polyethylene glycol PEG-EL). HalfLytely® in powder form for oral solution was reconstituted by adding water in the container provided, producing 2 liters of liquid. Subjects randomized to the HalfLytely®, a bisacodyl composition, treatment group began their treatment by taking two 5 mg bisacodyl tablets (according to approved labeled instruction) in the afternoon on the day prior to colonoscopy (Visit 2). After the first bowel movement or after 6 hours, whichever occurred first, subjects began to drink HalfLytely® at a rate of one 8 oz glass every 10 minutes. The HalfLytely® treatment group completed treatment 1 day before colonoscopy (Visit 2).

Compliance with treatment was documented in the case report form (CRF). Subjects were considered compliant if the dosing occurred within 30 minutes of the specified times. The following diet requirements and restrictions were followed for subjects enrolled in the study, regardless of treatment group: On the day before procedure, subjects were limited to a liquid diet only. Subjects received a subject diary card. For subjects with diabetes, special dietary instructions were provided.

Identity of Investigational Product(s)

PicoPrep™

PicoPrep™ powder for oral solution consisting of 2 sachets reconstituted and administered in divided doses. PicoPrep™ is a white crystalline powder for oral solution. Each sachet of PicoPrep™ contains: Sodium Picosulfate 10.0 mg, Magnesium Oxide, Light 3.5 gm, and Citric Acid, Anhydrous 12.0 gm. Magnesium oxide and citric acid react in solution to form magnesium citrate. PicoPrep™ was supplied in boxes containing 2 sachets each.

Physical Characteristics

PicoPrep™ exists in a white crystalline powder for oral solution. Each sachet consists of 4 layers: paper-polyethylene-aluminum-surlyn. Each pack contains a pair of sachets that can be separated by tearing apart the perforated strip. The weight of each sachet contents is 16.1 g.

Chemical Characteristics

Sodium picosulfate (an ingredient of PicoPrep™) is a bisphenol derivative, with the chemical name 4,4'-(2-pyridinylmethelene)-bisphenol-bis (hydrogen sulphate)(ester) disodium salt. The chemical formula is $C_{18}H_{13}NNa_2O_8S_2$ and the molar weight is 481.409 g/mol. The Systematic International Union of Pure and Applied Chemistry name of sodium picosulfate is: disodium 2-[bis(4-sulfonatooxyphenyl)methyl]pyridine.

The chemical formula of magnesium citrate (an ingredient of PicoPrep™ achieved during reconstitution of magnesium oxide and citric acid) is $C_{12}H_{10}Mg_3O_{14}$ and the molecular weight is 451.1 g/mol. Magnesium oxide has a solubility of 1 in 50 in water and is not soluble in alcohol.

Pharmaceutical Characteristics

The PicoPrep™ product sachets contain 10 mg sodium picosulfate, 3.5 g light magnesium oxide, and 12 g anhydrous citric acid. The second two active ingredients are widely used in pharmaceutical and food products, and both are USP grade ingredients. Magnesium citrate is listed as a saline laxative in the Food and Drug Administration (FDA) tentative over-the-counter (OTC) Monograph for laxatives (last update August 2006). Other excipients in the sachet are widely used in pharmaceutical and food products, and the majority also listed in the FDA database of Inactive Ingredients for Approved Drug Products.

The contents of each sachet are dissolved in approximately 150 ml water before taking. When added to water the magnesium oxide and citric acid combine to form magnesium citrate; this is an exothermic reaction and if the liquid becomes hot the patient is instructed to wait until it cools sufficiently to drink.

The drug substances are dissolved in solution before administration to the patient. They act locally within the intestinal tract and systemic absorption is minimal.

Summary

PicoPrep™ is a cathartic agent used to clean the bowel prior to X-ray examination, endoscopy or surgery. It is available as white crystalline powder with a faint odor of orange for oral solution. The active ingredients in PicoPrep™ are sodium picosulfate, a bisphenol derivative with the chemical name 4,4'-(2-pyridinylmethylene)-bisphenol-bis (hydrogen sulphate)(ester) disodium salt, and also light magnesium oxide and anhydrous citric acid. When the product is dispersed in water, the magnesium oxide and citric acid interact to form magnesium citrate, which is an osmotic laxative with a powerful cathartic effect. Citric acid is included in excess to ensure a complete effervescence reaction with potassium bicarbonate when dispersed in water. PicoPrep™ is provided in sachets containing 10 mg sodium picosulphate, 3.5 g light magnesium oxide, and 12 g anhydrous citric acid. PicoPrep™ treatment is administered as two doses taken 6 to 8 hours apart in the 24 hours prior to the hospital procedure.

In one embodiment, the picosulfate the bowel composition comprises sodium picosulfate, magnesium oxide, and citric acid. In some embodiments, the picosulfate bowel composition further comprises at least one additive. The at least one additive is chosen from pharmaceutically acceptable excipients, other active ingredients, flavors, sweeteners, colorings, and combinations thereof. In some embodiments, the first picosulfate bowel composition is prepared the day before the procedure. In other embodiments, the second picosulfate composition is prepared the day of the procedure.

Additionally, the picosulfate bowel composition can be a component of a picosulfate bowel composition kit. The picosulfate bowel composition kit may further comprise instructions for preparation of the picosulfate bowel composition for administration and/or administration of the composition.

HalfLytely®

HalfLytely® powder form for oral solution consisting of powder reconstituted for oral solution administered with two 5 mg bisacodyl tablets (according to approved labeled instruction). HalfLytely® is composed of 2 pink, round, enteric coated 5 mg bisacodyl delayed release tablets, stamped "BRA," and one 2-liter HalfLytely® bottle with powder for reconstitution (two 5 mg bisacodyl tablets+2 liters polyethylene glycol PEG-EL). HalfLytely® contains the active ingredients PEG-3350 (polyethylene glycol 3350) 210 gm, sodium chloride 5.6 gm, sodium bicarbonate 2.86 gm, and potassium chloride 0.74 gm. After adding 2 liters of water, the reconstituted HalfLytely® solution (clear and colorless) contains PEG-3350 31.3 mmol/L, sodium 65 mmol/L, chloride 53 mmol/L, bicarbonate 17 mmol/L, and potassium 5 mmol/L.

Lemon-lime HalfLytely® and Bisacodyl Tablets Bowel Prep Kit contains 1 gm lemon-lime flavoring ingredient. HalfLytely® is manufactured and supplied by Braintree Laboratories, Inc. Braintree, Mass. It is an approved GI lavage product indicated for cleansing of the colon as a preparation for colonoscopy in adults.

HalfLytely® is currently supplied to the US markets in one 2-liter bottle with powder for reconstitution and 2 bisacodyl tablets (two 5 mg bisacodyl tablets+2 liters polyethylene glycol PEG-EL). The HalfLytely® arm of this trial used the product commercially available in the United States.

Treatment Compliance

Preparations were given at the direction of the unblinded coordinator. The exact hour of administration varied according to the time of the procedure; therefore the coordinator who dispensed the drug instructed the subject about the exact time of administration during Visit 2.

Compliance with study drug was documented in the case report form. Subjects were considered compliant if dosing occurred within 30 minutes of the following specified timings:

Day before colonoscopy procedure:
 first reconstituted sachet: between 5:00 PM-9:00 PM
Day of colonoscopy procedure:
 second reconstituted sachet: 5 hours prior to but no later than 9 hours prior to procedure Assessments, Endpoints, and Appropriateness of Measurements Assessments The primary variable was: The Aronchick Scale for demonstration of non-inferiority of PicoPrep™ to HalfLytely® in efficacy of overall colon cleansing in preparation for colonoscopy.

The secondary variables were: (1) The Ottawa Scale for demonstration of non-inferior of PicoPrep™ to HalfLytely® in efficacy of ascending colon cleansing. (2) Fluid assessment. (3) A standardized subject questionnaire for determination of tolerability and satisfaction of the preparation. (4) Monitoring of AEs, collection of concomitant medications, physical examination including weight and orthostatic vital signs (blood pressure and pulse rate), ECG findings, and clinical laboratory tests including change from baseline, for determination of safety.

Efficacy Assessments

Aronchick Scale

Using the Aronchick Scale for the primary efficacy assessment of the preparation, the gastroenterologist performing the evaluation of overall colon cleansing was blinded to treatment. Table 1 provides grades of overall colon cleansing and their definitions. A subject was considered a "responder" if overall colon cleansing was excellent or good on this 4-point scale.

TABLE 1

Aronchick Scale

| Grade | Description |
| --- | --- |
| Excellent | >90% of mucosa seen, mostly liquid stool, minimal suctioning needed for adequate visualization |
| Good | >90% of mucosa seen, mostly liquid stool, significant suctioning needed for adequate visualization |
| Fair | >90% of mucosa seen, mixture of liquid and semisolid stool, could be suctioned and/or washed |
| Inadequate | <90% of mucosa seen, mixture of semisolid and solid stool which could not be suctioned or washed |

Ottawa Scale

Using the Ottawa Scale for the secondary efficacy assessment of the preparation, the gastroenterologist performing the evaluation of cleansing of the ascending colon was blinded to treatment. In addition to the ascending colon, data for the mid (transverse, descending) colon, and the descending (recto-sigmoid) colon were graded 0, 1, 2, 3 or 4 according to the definitions in Table 2.

TABLE 2

Ottawa Scale (Cleanliness)

| Grade | Description |
| --- | --- |
| 0 | Excellent: Mucosal detail clearly visible. If fluid is present, it is clear. Almost no stool residue. |
| 1 | Good: Some turbid fluid or stool residue but mucosal detail still visible. Washing and suctioning not necessary. |
| 2 | Fair: Turbid fluid or stool residue obscuring mucosal detail. However, mucosal detail becomes visible with suctioning. Washing not necessary |
| 3 | Poor: Presence of stool obscuring mucosal detail and contour. However, with suctioning and washing, a reasonable view is obtained. |
| 4 | Inadequate: Solid stool obscuring mucosal detail and contour despite aggressive washing and suctioning. |

The score of all colon segments was evaluated as

Clinical Success: 0, 1, or 2 score in the ascending colon

Not a Clinical Success: Presence of 3 or 4 score in the ascending colon

Subject's Tolerability and Satisfaction Questionnaire

A standard questionnaire was used to assess subjects' tolerability and satisfaction and compared the treatment groups. This questionnaire was administered to subjects by the study site coordinator at Visit 3 prior to sedation for the colonoscopy.

The questions were:
1. How easy or difficult was it to consume the study drug?
2. Were you able to consume the entire prep as instructed?
3. Please describe your overall experience of the study preparation:
4. The taste of this study preparation was:
5. Would you ask your doctor for this preparation again if you need another colonoscopy in the future?
6. Would you refuse the same preparation again if it were to be prescribed to you in the future?
7. Have you had a colonoscopy before (within the past 3 years)?
   7a. If yes, which type of colon cleansing medication(s) did you receive?
   7b. If yes, provide the name of the colon cleansing medication used in most recent colonoscopy:
   7c. If yes, do you remember if you were able to complete as instructed the entire colon cleansing medication you used in you most recent colonoscopy?
   7d. If yes, would you describe the colon cleansing medications you received for this colonoscopy as? (1: Much better - - - 5: Much worse)

Safety Assessments

Safety variables included:

Medical history and demographic data

Physical examination

Weight and orthostatic vital signs (including blood pressure and pulse rate)

12-lead ECGs

Clinical laboratory tests including urinalysis

Incidence, severity, and causality of AEs/serious adverse events (SAEs)

Concomitant medication reporting

Efficacy Results and Tabulations of Individual Subject Data

Primary Efficacy Variable: Aronchick Scale

The primary efficacy variable was the percentage of subjects classified as responders (successes), where responder is a subject who had a rating of Excellent or Good on the Aronchick scale at Visit 3 during colonoscopy.

The percentage of responders was similar in both the intent-to-treat and the per protocol analysis sets and consistently greater in the PicoPrep™ than the HalfLytely® treatment group in both analysis sets.

In both analysis sets, the difference between PicoPrep™ and HalfLytely® satisfied the criteria for non-inferior of PicoPrep™ versus HalfLytely® in response rates; subsequently, the lower bound of the CI was determined, and the superiority of PicoPrep™ was declared.

Secondary Efficacy Endpoints

The secondary efficacy variables were the percentage of subjects classified as responders (successes), where responder is a subject who had a rating of Excellent, Good, or Fair on the Ottawa Scale at Visit 3 during colonoscopy by section of the colon (ascending colon, mid colon, and recto-sigmoid colon) and overall, as well as fluid assessment (small, moderate, or large amount), and a standardized subject questionnaire for determination of tolerability and satisfaction of the preparation.

The secondary analyses using the Ottawa Scale for ascending colon cleansing were consistent with the results of the primary analysis; PicoPrep™ was found to be non-inferior to HalfLytely®. Additionally, in all sections of the colon, PicoPrep™ was found to be superior to HalfLytely®. Further, in the fluid assessment and across the subject questionnaire for the determination of tolerability and satisfaction of the preparation, PicoPrep™ demonstrated statistically "better" results when compared with HalfLytely®.

Colonoscopy Timing

The Study's primary and secondary objectives sought to demonstrate non-inferiority and assess safety, efficacy, and tolerability. Additionally, it was discovered that with the picosulfate composition (i.e., PicoPrep™), a minimal time interval could be achieved between the last ingestion of the picosulfate composition and the performance of the colonoscopy.

Although the study protocol for PicoPrep™ proscribed administration of the second reconstituted sachet at least 5 hours prior to but no later than 9 hours prior to colonoscopy, deviations in time administration occurred. Those deviations included the administration of PicoPrep™ less than 5 hours prior to the colonoscopy procedure.

In some instances, administration occurred less than or equal to 4 hours prior to the colonoscopy procedure, e.g., less than about 4 hours, less than about 3 hours, less than about 2 hours and further for example, a time interval ranging from about 4 hours to about 1 hour, from about 3 hours to about 1 hour, from about 2 hours to about 1 hour, from about 3 hours to about 2 hours, prior to the colonoscopy, or any half hour interval in between. Despite the deviations in time from administration, patients still responded with PicoPrep™ under the Aronchick scale. Table 3 below provides the data for those patients that were administered PicoPrep™ less than or equal to 4 hours prior to the colonoscopy procedure. Table 4 below summaries the data for those patients that were administered PicoPrep™ at time intervals according to the protocol.

TABLE 3

Time from Last Dose of Treatment to Start of Colonoscopy and Response

| Patient Identification | Treatment | Time From Last Dose of Treatment to Start of Colonoscopy (hours) | Response |
|---|---|---|---|
| 150 | PicoPrep ™ | 3.67 | Responder |
| 461 | PicoPrep ™ | 1.78 | Responder |

Responder = If "Good" or "Excellent" designation of overall colon cleansing, based on the Aronchick Scale

TABLE 4

Summary of Responders and Non-responders for Various Time Intervals with PicoPrep ™

| Response (Responder or Non-responders) | Time Interval | Number of Patients |
|---|---|---|
| Responders | <=4 hours | 2 |
| Responders | >4 hours | 490 |
| Responders | <=6 hours | 74 |
| Responders | >6 hours | 418 |
| Non-responders | <=4 hours | 0 |
| Non-responders | >4 hours | 96 |
| Non-responders | <=6 hours | 10 |
| Non-responders | >6 hours | 86 |

Responder = If "Good" or "Excellent" designation of overall colon cleansing, based on the Aronchick Scale II. PicoPrep™ Split-Dose v. PicoPrep™ Day Before Dose Study Overall Clinical Study and Design: A randomized, assessor-blinded, multi-centered study investigated the efficacy, safety and tolerability of "Split-Dose" sodium picosulfate, magnesium oxide, and citric acid for oral administration, for example PicoPrep™ or Pico-Salax®, versus "Day Before" of the same product for colon cleansing in preparation for colonoscopy.

The study was conducted at one investigative site in Canada. It was planned that a sufficient number of subjects would be screened to ensure up to 16 randomized subjects (8 subjects to each treatment group).

Subjects having elective colonoscopy who fulfilled all inclusion and no exclusion criteria were randomized to one of two treatment groups ((1)split-dose group or (2) day-before group) at Visit 2. On the day before the procedure (24 hours before), all subjects were limited to a liquid diet only. All assessments were performed at Visit 3 occurring less than 5 days from Visit 2.

(1) Split-Dose Group: Subjects randomized to the split-dose group began treatment ($1^{st}$ reconstituted sachet) on the day before colonoscopy between 5:00 and 9:00 PM, and completed the treatment ($2^{nd}$ reconstituted sachet) the next day, at least 2 hours, but no later than 4 hours, prior to colonoscopy.

(2) Day-Before Group: Subjects randomized to the day-before group began treatment ($1^{st}$ reconstituted sachet) one day before colonoscopy between 4:00 and 6:00 PM, and completed the treatment ($2^{nd}$ reconstituted sachet) at least 6 hours later, between 10:00 PM and 12:00 AM.

Sachets were reconstituted by mixing the contents of the sachet in a cup with approximately 5 oz. of cold water. Following each administration subjects consumed five 8 oz. glasses of clear liquids after the first administration and three 8 oz. glasses of clear liquids after the second administration.

Treatment Compliance

As in the study discussed above, preparations were given at the direction of the unblinded coordinator. The exact hour of administration varied according to the time of the procedure; therefore the coordinator who dispensed the drug instructed the subject about the exact time of administration during Visit 2.

Compliance with study drug was documented in the case report form. Subjects were considered compliant if dosing occurred within 30 minutes of the specified times.

Assessments, Endpoints, and Appropriateness of Measurements

Assessments, endpoints, and appropriateness of measurements were the same as discussed above.

Colonoscopy Timing

The Study's primary and secondary objectives sought to demonstrate non-inferiority and assess safety, efficacy, and tolerability with regard to the minimal time interval achieved between the last ingestion of the picosulfate composition and the performance of the colonoscopy discussed above.

Efficacy Conclusions

This study examined the efficacy, patient tolerability, and safety of sodium picosulfate, magnesium oxide, and citric acid for oral administration, for example PicoPrep™ or Pico-Salax®, when given as two doses the "Day Before" compared to a "Split Dose" regimen where the second dose was given less than 4 hours to the scheduled time of colonoscopy. The study demonstrated that both dosing regimens were feasible and effective.

The Study enrolled 16 subjects between the ages of 47 and 74 comprising 11 males and 5 females, all of which completed the study. There were no major protocol deviations. One patient took his second dose at a 4 hour interval as opposed to 6 hours. All patients were included in the analysis.

The primary efficacy variable was the percentage of subjects classified as responders (successes), where responder is a subject who had a rating of Excellent or Good on the Aronchick scale at Visit 3 during colonoscopy. See Table 5.

TABLE 5

Summary of Responders and Non-responders

| Treatment Group | Total Patients | No. of Responders | No. of Non-Responders |
|---|---|---|---|
| Split-Dose | 8 | 5 | 3 |
| Day Before | 8 | 4 | 4 |

Responder = If "Good" or "Excellent" designation of overall colon cleansing, based on the Aronchick Scale Of the eight patients randomized to the "Split Dose" group, five patients were classified as responders, four of which were rated as excellent and one as good on the Aronchick scale. Of eight patients randomized to the "Day Before" group, four were classified as responders, all which were classified as good on the Aronchick scale and none as excellent.

The evaluation of the efficacy of the preparation using the Aronchick score showed that there was a trend towards better cleansing with the "split dose" (4 preparations deemed excellent vs. 0 in the "day--before" dosing group) but this did not reach statistical significant. See Table 6. This may represent a type II error as the sample size is small. There was also a significant improvement in the right colon cleansing using the Ottawa Bowel Preparation Score which supports this contention. See Table 6. Previous studies showed that split dosing can provide improved cleansing, particularly if the colonoscopy is performed in the afternoon i.e. the procedure is further from the last dose of the cleansing agent. Nonetheless, none of the dosing schedules employed in the current study were scored as inadequate suggesting both regimens have efficacy.

TABLE 6

Summary of Ottawa Bowel Preparation Scores and Aronchick scores.

| Study ID # | Randomization | Procedure completed | OBP right colon | OBP mid colon | OBP recto-sigmoid | Fluid Score | Total OBP score | ABP Score |
|---|---|---|---|---|---|---|---|---|
| 1 | 1 | 1 | 3 | 3 | 0 | 1 | 7 | 2 |
| 2 | 2 | 1 | 2 | 2 | 2 | 1 | 7 | 1 |
| 3 | 1 | 1 | 3 | 2 | 2 | 1 | 8 | 2 |
| 4 | 2 | 1 | 3 | 3 | 3 | 2 | 11 | 3 |
| 5 | 2 | 1 | 2 | 2 | 2 | 1 | 7 | 1 |
| 6 | 1 | 1 | 3 | 3 | 2 | 1 | 9 | 3 |
| 7 | 2 | 1 | 3 | 2 | 1 | 0 | 6 | 3 |
| 8 | 1 | 1 | 3 | 3 | 3 | 0 | 9 | 3 |
| 9 | 2 | 1 | 2 | 2 | 1 | 0 | 5 | 1 |
| 10 | 1 | 1 | 3 | 2 | 2 | 0 | 7 | 2 |
| 11 | 1 | 1 | 4 | 1 | 1 | 0 | 6 | 3 |
| 12 | 2 | 1 | 2 | 1 | 2 | 0 | 5 | 1 |
| 13 | 2 | 1 | 3 | 2 | 2 | 0 | 7 | 2 |
| 14 | 1 | 1 | 3 | 2 | 3 | 0 | 8 | 3 |
| 15 | 2 | 1 | 3 | 2 | 3 | 1 | 9 | 3 |
| 16 | 1 | 1 | 3 | 2 | 3 | 0 | 8 | 2 |

Table Designations:
OBP = Ottawa Bowel Prep Scale;
ABP = Aronchick Bowel Prep Scale;
Randomization (1 = day before 2 = split dose);
Procedure completed (1 = yes; 2 = no due to poor prep; and 3 = no due to other reason);
OBP right colon (0 = excellent; 1 = good; 2 = fair; 3 = poor; 4 = inadequate);
OBP mid colon (0 = excellent; 1 = good; 2 = fair; 3 = poor; 4 = inadequate);
OBP recto-sigmoid (0 = excellent; 1 = good; 2 = fair: 3 = poor: 4 = inadequate);
Fluid Score (0 = small; 1 = moderate: 2 = large);
ABP Score (1 = excellent; 2 = good; 3 = fair; 4 = inadequate)

Primary End Points

There was a trend towards a better Aronchick score for the split dose group mean and standard deviation (mean±standard deviation=1.88±0.991; 4/8 reported as excellent); compared to the day before group (mean±standard deviation=2.5±0.535; 0/8 reported excellent) but this was not significant when analyzed using a Mann Whitney test.

Secondary End Points

There was no difference in the overall Ottawa bowel preparation score for the "split dose" group compared to the "day-before" group. The right colon (ascending colon) scores were significantly better in the "split dose" group (p=0.015).

Adverse Events

No serious adverse events were reported to nurse or physicians. There were no clinically significant changes in physiological (postural vital signs) or biochemical parameters, including changes in creatinine, sodium, potassium, or magnesium. There was no difference in the reporting of symptoms between the "day-before" group and the "split dose" group.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of timing a colonoscopy procedure performed on a patient in need thereof, comprising:
   administering a picosulfate bowel composition to the patient; and
   performing the colonoscopy procedure from about 3 hours to about 1 hour after the administration of the picosulfate bowel composition.

2. The method according to claim 1, wherein the step of performing the colonoscopy procedure occurs from about 3 hours to about 2 hours after the administration of the picosulfate bowel composition.

3. The method according to claim 1, wherein the picosulfate bowel composition is prepared from a mixture comprising sodium picosulfate, magnesium oxide, and citric acid.

4. The method according to claim 1, further comprising administering clear liquids to the patient following the administration of the picosulfate bowel composition.

5. The method according to claim 1, wherein the picosulfate bowel composition is part of a picosulfate bowel composition kit further comprising instructions for preparing the picosulfate bowel composition for administration.

6. A method of timing a colonoscopy procedure performed on a patient in need thereof, comprising:
   administering a first picosulfate bowel composition to the patient the day before the colonoscopy procedure;
   administering a second picosulfate bowel composition to the patient on the day of the colonoscopy procedure; and
   performing the colonoscopy procedure from about 3 hours to about 1 hour after the administration of the second picosulfate bowel composition.

7. The method according to claim 6, wherein the step of performing the colonoscopy procedure occurs from about 3 hours to about 2 hours after the administration of the second picosulfate bowel composition.

8. The method according to claim 6, wherein the first and the second picosulfate bowel compositions are each prepared from a mixture comprising sodium picosulfate, magnesium oxide, and citric acid.

9. The method according to claim 6, further comprising administering clear liquids to the patient following at least one of the first and the second administrations of the picosulfate bowel compositions.

10. The method according to claim 6, wherein the first and second picosulfate bowel compositions are part of a picosulfate bowel composition kit further comprising instructions for preparing the picosulfate bowel compositions for administration.

11. A method of timing a colonoscopy procedure performed on a patient in need thereof, the method consisting essentially of:
   administering a first picosulfate bowel composition to the patient on the day before the colonoscopy procedure; and
   administering a second picosulfate bowel composition to the patient on the day of the colonoscopy procedure from about 3 hours to about 1 hour prior to the colonoscopy procedure, and
   optionally administering clear liquids to the patient following the least one of the first and second administrations of the picosulfate bowel compositions.

12. The method according to claim 11, wherein the step of administering the second picosulfate bowel composition occurs from about 3 hours to about 2 hours prior to the procedure.

13. The method according to claim 11, wherein the first and the second bowel compositions are prepared from a mixture comprising sodium picosulfate, magnesium oxide, and citric acid.

14. The method according to claim 11, further comprising administering clear liquids to the patient following at least one of the first and the second administrations of the bowel compositions.

15. The method according to claim 11, wherein the first and second picosulfate bowel compositions are part of a picosulfate bowel composition kit further comprising instructions for preparing the picosulfate bowel compositions for administration.

16. The method according to claim 1, wherein the picosulfate bowel composition comprises sodium picosulfate and magnesium citrate.

17. The method according to claim 6, wherein the first and second picosulfate bowel compositions each comprise sodium picosulfate and magnesium citrate.

18. The method according to claim 11, wherein the first and second picosulfate bowel compositions each comprise sodium picosulfate and magnesium citrate.

19. The method according to claim 16, wherein the bowel composition is prepared from a mixture comprising sodium picosulfate, magnesium oxide, and citric acid.

20. The method according to claim 16, wherein the method comprises administering clear liquids to the patient after administering the picosulfate bowel composition.

21. The method according to claim 17, wherein the first and second picosulfate bowel composition are each prepared from a mixture comprising sodium picosulfate, magnesium oxide, and citric acid.

22. The method according to claim 17, wherein the method comprises administering clear liquids to the patient after administering the first picosulfate bowel composition, after administering the second picosulfate bowel composition, or both.

23. The method according to claim 18, wherein the first and second picosulfate bowel composition are each prepared from a mixture comprising sodium picosulfate, magnesium oxide, and citric acid.

24. The method according to claim 18, wherein the method comprises administering clear liquids to the patient after administering the first picosulfate bowel composition, after administering the second picosulfate bowel composition, or both.

* * * * *